United States Patent [19]

Benner

[11] Patent Number: 4,601,882
[45] Date of Patent: Jul. 22, 1986

[54] OXYGEN ANALYZER

[75] Inventor: William H. Benner, Danville, Calif.

[73] Assignee: The United States of America as represented by the United States Department of Energy, Washington, D.C.

[21] Appl. No.: 608,282

[22] Filed: May 8, 1984

[51] Int. Cl.[4] ............................................. G01N 31/12
[52] U.S. Cl. ........................................ 422/80; 422/78; 436/127; 436/155; 436/157
[58] Field of Search ..................... 422/78, 80; 436/127, 436/136, 138, 155, 157

[56] References Cited

U.S. PATENT DOCUMENTS

| | | | |
|---|---|---|---|
| 1,515,237 | 11/1924 | Yensen | 436/158 X |
| 2,731,330 | 1/1956 | Codell et al. | 422/78 X |
| 2,774,588 | 12/1956 | Oita | 422/78 |
| 3,252,759 | 5/1966 | Simon | 422/78 X |
| 3,298,786 | 1/1967 | Hinsvark | 422/78 X |
| 3,374,064 | 3/1968 | Kolsto | 422/78 |
| 3,647,385 | 3/1972 | Stephens | 436/155 |
| 3,703,355 | 11/1972 | Takahashi et al. | 422/78 X |
| 3,847,546 | 11/1974 | Paul | 422/78 X |
| 3,861,874 | 1/1975 | Kre | 422/80 X |
| 3,945,799 | 3/1976 | Honma | 422/78 X |
| 4,229,412 | 10/1980 | Orths et al. | 422/78 X |
| 4,244,917 | 1/1981 | Woods et al. | 422/78 |
| 4,332,770 | 6/1982 | Ishida et al. | 422/78 |

OTHER PUBLICATIONS

Benner et al., "Determination of Organic Oxygen in Ambient Particulate Matter", LBL-16103, University of California, Aug. 1983.

Uhdeova et al., Analytical Chemistry, vol. 53, pp. 164–167, 1981.

Campanile et al., Analytical Chemistry, vol. 23, No. 10, pp. 1421–1426, Oct. 1951.

Oita et al., Analytical Chemistry, vol. 26, No. 3, pp. 600–602, Mar. 1954.

Primary Examiner—Arnold Turk
Assistant Examiner—Robert J. Hill, Jr
Attorney, Agent, or Firm—L. E. Carnahan; Roger S. Gaither; Judson R. Hightower

[57] ABSTRACT

An oxygen analyzer which identifies and classifies micrograms quantities of oxygen in ambient particulate matter and for quantitating organic oxygen in solvent extracts of ambient particulate matter. A sample is pyrolyzed in oxygen-free nitrogen gas ($N_2$), and the resulting oxygen quantitatively converted to carbon monoxide (CO) by contact with hot granular carbon (C). Two analysis modes are made possible: (1) rapid determination of total pyrolyzable oxygen obtained by decomposing the sample at 1135° C., or (2) temperature-programmed oxygen thermal analysis obtained by heating the sample from room temperature to 1135° C. as a function of time. The analyzer basically comprises a pyrolysis tube containing a bed of granular carbon under $N_2$, ovens used to heat the carbon and/or decompose the sample, and a non-dispersive infrared CO detector coupled to a mini-computer to quantitate oxygen in the decomposition products and control oven heating.

13 Claims, 2 Drawing Figures

OXYGEN ANALYZER

The invention described herein arose in the course of, or under, Contract No. DE-AC03-76SF00098 between the United States Department of Energy and the University of California.

BACKGROUND OF THE INVENTION

The invention relates to analyzing gaseous and solid materials, particularly components containing oxygen, and more particularly to an oxygen analyzer capable of identifying and classifying microgram quantities of oxygen in ambient particulate matter.

Numerous methods and apparatus have been developed for the analysis of matter, particularly by different types of pyrolysis ovens utilizing various types of sample holding structures and product evaluation techniques. These prior known approaches are exemplified by U.S. Pat. No. 1,515,237 issued Nov. 11, 1924 to T. D. Yensen; U.S. Pat. No. 3,252,759 issued May 24, 1966 to W. Simon; U.S. Pat. No. 3,374,064 issued Mar. 19, 1968 to O. L. Kolsto; U.S. Pat. No. 3,861,874 issued Jan. 21, 1975 to A. E. Krc; and U.S. Pat. No. 4,244,917 issued Jan. 13, 1981 to R. A. Woods et al.

More recently there has been an increased interest in determining the content of ambient particulate matter. The particulate matter is collected by filter sampling methods well known in the art and then analyzed to determine the components in the particulate matter, as well as a quantitative assessment of the components.

Ambient aerosol particles, complex mixtures of organic and inorganic chemical compounds, can yield information on the aerosol origins and atmospheric transformations when speciated. The major anthropogenic species are compounds of carbon, hydrogen, oxygen, nitrogen, and sulfur. Of these compounds, oxygen has traditionally been the most difficult to analyze, requiring a complex procedure or special apparatus to perform the analysis. There are currently two known and established aerosol compound speciation procedures, either of which may be used in analyzing devices.

The most common of these two processes involves a system in which a weighed sample is placed in a quartz pyrolysis tube containing platinized carbon. Oxygen in the gaseous combustion products are converted to carbon monoxide by passage through the platinized carbon and the carbon monoxide is subsequently oxidized to carbon dioxide by passage over copper oxide. The sample is pyrolyzed in a helium atmosphere so that carbon monoxide is formed from oxygen in the sample and so that the platinized carbon does not burn. The carbon monoxide is oxidized by the copper oxide to form carbon dioxide, which is detected and measured, giving the total oxygen concentration in the sample. This procedure or process may, for example, be carried out in a Perkin-Elmer Model 240 Elemental Analyzer made by Perkin-Elmer Corp., Norwalk, Conn., which incorporates features of above-referenced U.S. Pat. No. 3,252,759.

The other of these procedures or processes uses the normal inert gas-fusion method as a basis for determining oxygen released at successively higher temperatures. The sample is heated in a graphite crucible, current is increased in discrete steps using a program tailored for the specific oxides believed to be present. The oxygen peaks are plotted against temperature on an integral printer, yielding information about individual compounds present in the sample. This process may, for example, be carried out in a LECO RO-16 Oxygen Determinator, made by LECO Corp., St. Joseph, Mich.

While the above-referenced processes and apparatus have been effective, they have been found to lack the necessary sensitivity for certain types of analysis. Thus, a need exists for an oxygen analysis procedure and apparatus which provides greater sensitivity than the currently known approaches.

SUMMARY OF THE INVENTION

It is an object of this invention to provide a technique and apparatus for determining microgram quantities of oxygen in samples of ambient particulate matter and to quantitate organic oxygen in solvent extracts of ambient particulate matter.

A further object of the invention is to provide an oxygen analyzer which has greater sensitivity than known analysis methods and apparatus.

A still further object of the invention is to provide a device for analyzing the components of a particulate matter having sensitivity estimated to be up to two times that of any known particulate matter analyzing device.

Another object of the invention is to provide a method of identifying and classifying microgram quantities of oxygen in ambient particulate matter, wherein a sample of the particulate matter is pyrolyzed in oxygen-free $N_2$, the resulting oxygen is quantitatively converted to carbon monoxide (CO) by contact with hot granular carbon, and the evolved CO is detected by non-dispersed infrared spectrometry.

Another object of the invention is to provide an oxygen analyzer for determining microgram quantities of oxygen from a sample of material, which basically comprises a pyrolysis tube containing a bed of granular carbon in which the sample is thermally decomposed under $N_2$, a plurality of ovens used to heat the carbon and/or decompose the sample, and a non-dispersed infrared CO detector coupled to a small computer to quantitate oxygen in the decomposition products. Using this plurality of ovens, oxygen in the sample can be determined as a function of sample temperature.

Other objects of the invention will become readily apparent to those skilled in the art from the following description and the accompanying drawings.

DETAILED DESCRIPTION OF THE INVENTION

The present invention involves a pyrolysis technique and apparatus by which microgram quantities of oxygen in ambient particulate matter can be determined. A sample of the particulate matter is pyrolyzed in oxygen-free nitrogen gas ($N_2$). The oxygen resulting from this pyrolysis is quantitatively converted to carbon monoxide (CO) by contact with hot (1135° C.) granular carbon. The evolved CO is detected by non-dispersed infrared spectrometry (NDIR) or detected by carbon dioxide ($CO_2$) coulometry after oxidation to $CO_2$. Two modes of analysis are possible with the technique and apparatus of this invention. One mode involves a rapid determination of total pyrolyzable oxygen which is obtained by decomposition and conversion of all oxygen-containing species to CO in the same tube furnace or oven maintained at 1135° C. The other mode involves temperature-programmed oxygen thermal analysis which is obtained by heating a sample from room temperature to 1135° C. at 30° C./min. sequences, for example, and then forcing the decomposition products through the hot carbon maintained at 1135° C. in a separate furnace or oven. Oxygen thermograms of the samples can be obtained by use of the temperature-programmed mode, as described hereinafter, and such thermograms can be used, for example, to quantitate organic oxygen in solvent extracts of ambient particulate matter.

Figure 1:
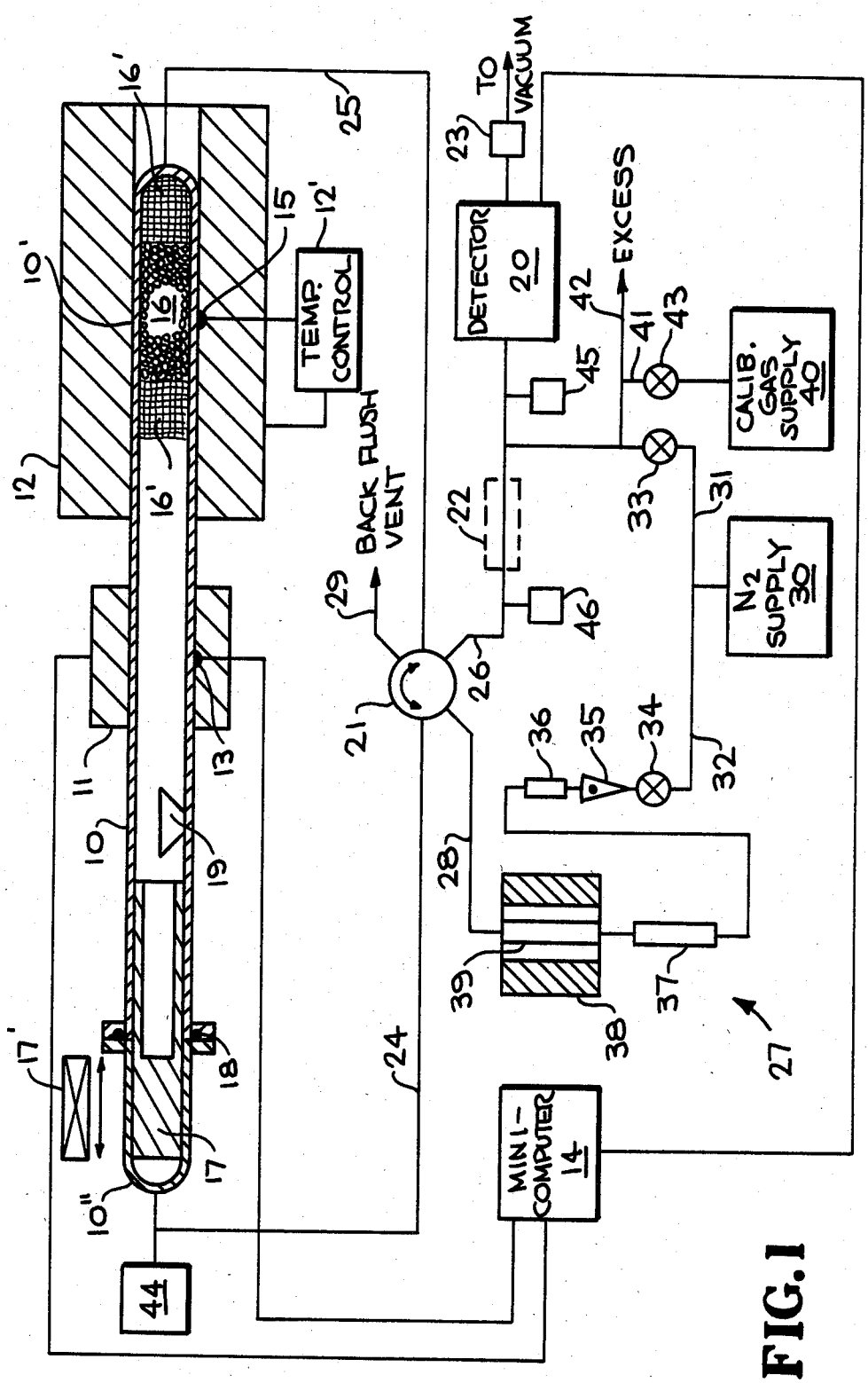
FIG. 1 schematically illustrates an embodiment of an analytical apparatus for quantitating pyrolyzable oxygen and obtaining oxygen thermograms in accordance with the invention.

Referring now to the drawings, the embodiment of the invention illustrated in FIG. 1 basically comprises a quartz pyrolysis tube 10 having sections thereof surrounded by a temperature-programmed oven or furnace 11 and a pyrolysis oven or furnace 12. Oven 11 is provided with a thermocouple 13 connected to a mini-computer 14. Oven 12 is provided with a thermocouple 15 connected to a temperature controller 12' which maintains oven 12 at the desired temperature. A quantity of granular carbon 16 is located in a reduced diameter end section 10' of pyrolysis tube 10 with the carbon 16 being enclosed by plugs 16' of quartz wool, for example, located at each end of tube section 10'. Oven 12 is controlled to maintain the carbon 16 at 1135° C. A magnetic plunger mechanism, generally indicated at 17, is removably secured to and extends into the opposite (inlet) end of pyrolysis tube 10 via a coupling having 0-rings 18. Tube 10 includes an end section 10" within which the base of magnetic plunger mechanism 17 is mounted. A boat 19, constructed of platinum, for example, for holding a sample to be analyzed is located in pyrolysis tube 10 and adapted to be moved by the magnetic plunger 17 into oven 11 or oven 12. While not shown, the magnetic plunger 17 is activated and controlled by a permanent magnet arrangement, generally indicated at 17', which causes movement of the plunger within the pyrolysis tube 10, as indicated by the double arrow. The details of such magnetic mechanisms are known in the art and do not constitute part of this invention, and thus such mechanism is generally referred to herein.

A non-dispersed infrared (NDIR) CO detector 20 is directly coupled to mini-computer 14 and connected to oven 12 via a multiport valve 21. The detector 20 could be modified to function as a $CO_2$ detector in applications where the CO is detected by $CO_2$ coulometry after oxidation to $CO_2$. This would be accomplished by inserting between valve 21 and detector 20, a CO oxidation filter or mechanism indicated at 22 and composed of iodine pentoxide ($I_2O_5$). Detector 20 is connected to vacuum, indicated by legend, via an orifice 23.

The multiport valve 21 is constructed so as to be selectively connected: 1) to magnetic plunger 17 and the inlet end of pyrolysis tube 10 via conduit or tubing 24, 2) to the granular carbon 16 contained in tube section 10' within oven 12 via conduit or tubing 25, 3) to the detector 20 via conduit or tubing 26, 4) to a scrubber and filter assembly, generally indicated at 27, via conduit or tubing 28, and 5) to a backflush vent 29. A nitrogen gas ($N_2$) supply 30 is connected to conduit 26 and to the scrubber and filter assembly 27 via conduits 31 and 32, respectively, each of which are provided with needle valves 33 and 34, respectively. The scrubber and filter assembly 27 consists of a series of components comprising a rotameter 35 connected to conduit 32, a filter 36 composed of magnesium perchlorate (Mg $(ClO_4)_2$), a filter 37 composed of phosphorus pentoxide ($P_2O_5$) on glass beads, and an oven 38 in which is heated a quantity of copper (Cu), indicated at 39, to a temperature of 325°, which is connected to conduit 28. Thus, $N_2$ from supply 30 may be directed to multiport valve 21 via conduit 32, needle valve 34, scrubber and filter assembly 27, and conduit 28, or via conduit 31, needle valve 33, and conduit 26. Also, a supply of calibration gas 40, such as 40 ppm CO in $N_2$, is connected via conduits 41 and 42 to conduit 31, with a needle valve 43 located in conduit 41, and with conduit 42 being also connected to an exhaust by which any excess gas is discharged, as indicated by legend.

For system checkout, injection of a known quantity of a known material or gas is inserted into pyrolysis tube 10 and/or detector 20. This is accomplished via septums 44, 45 or 46 containing the selected known gas and which are respectively connected in conduits 24 and 26, with septum 46 being located between valve 21 and CO oxidation filter 22 for $CO_2$ detection checkout when utilized.

The above-described oxygen analyzer is able to determine the concentration of pyrolyzable oxygen in filter samples of atmospheric particulate matter that pyrolyzes below 1135° C. This excludes alumina ($Al_2O_3$) and silica ($SiO_2$), but includes carbonates, some metal oxides, nitrates, organic oxygen, silicates, sulfates, water and adsorbed gases like $CO_2$ and $O_2$. In addition OH functional groups on the surface of many siliceous materials will decompose below 1135° C.

In operation of the illustrated apparatus, CO or $CO_2$ samples are injected via septums 44 or 45 to check the performance of the detector 20. Also, septum 44 may be activated to test the conversion of oxygen to CO in oven 12. A filter sample to be analyzed is placed in boat 19 and loaded into the cool zone (inlet) of the pyrolysis tube 10 during backflushing of the tube with $N_2$. The loading of boat 19 is accomplished by removal of the magnetic plunger 17 and boat 19 from the tube 10, placing the sample on the boat, inserting the boat within the tube 10, and resealing the tube. Backflushing with $N_2$ from supply 30 is carried out by directing selected amounts of $N_2$ through conduits 31 and 32 via needle valves 33 and 34 and conduits 26 and 28, respectively, through multiport valve 21 which is positioned to interconnect conduits 26 and 28 with conduit 25 which directs the oxygen-free $N_2$ into pyrolysis tube 10, whereafter the valve 21 is positioned to interconnect conduit 24 with backflush vent 29, whereby entrained air is backflushed from tube 10. By way of example, 40 ml/min of $N_2$ is directed through filter and scrubber assembly 27 while 1 l/min of $N_2$ is directed into conduit 26. The advantages of this mixed flow of $N_2$ is to decrease the residence time of CO in the NDIR detector.

By activation of magnetic plunger mechanism 17, sample containing boat 19 is slid through pyrolysis tube 10 into either of ovens 11 or 12. Depending on which oven the sample containing boat 19 is placed in, oxygen analysis can be performed optionally by one of the two above described modes. However, in the analysis by either mode, oven 12 is maintained at 1135° C. to heat the carbon 16 for converting any oxygen in oven 12 to CO. If the sample is place in oven 12 which is maintained at 1135° C., the sample undergoes decomposition by pyrolysis and conversion of all oxygen-containing gases to CO by contact with the hot (1135° C.) granular carbon 16, all within oven 12, and the CO is directed via valve 21 into detector 20. Thus, if the sample is placed directly in oven 12, the pyrolyzable oxygen (Op) is quantitated. If the sample containing boat is placed in the temperature-programmable oven 11, wherein the temperature is increased from room temperature to 1135° C. in timed increments (30° C. increase per min. for example), decomposition of the sample is obtained as a function of temperature and time. The decomposition products from oven 11 are forced through oven 12 wherein the oxygen is converted to CO as above described and the evolved CO is detected and the amount determined via detector 20. The electronic signal produced by detector 20 is processed by mini-computer 14 in successive time intervals so that the concentration of CO entering detector 20 is stored in memory as a function of time.

Mini-computer 14 is also used to control the temperature programmed oven 11. An electrical signal from thermocouple 13 is used in a feedback circuit to control electrical power for heating oven 11. In this fashion, a 30° C./min increase in temperature in oven 11 is obtained.

Figure 2:
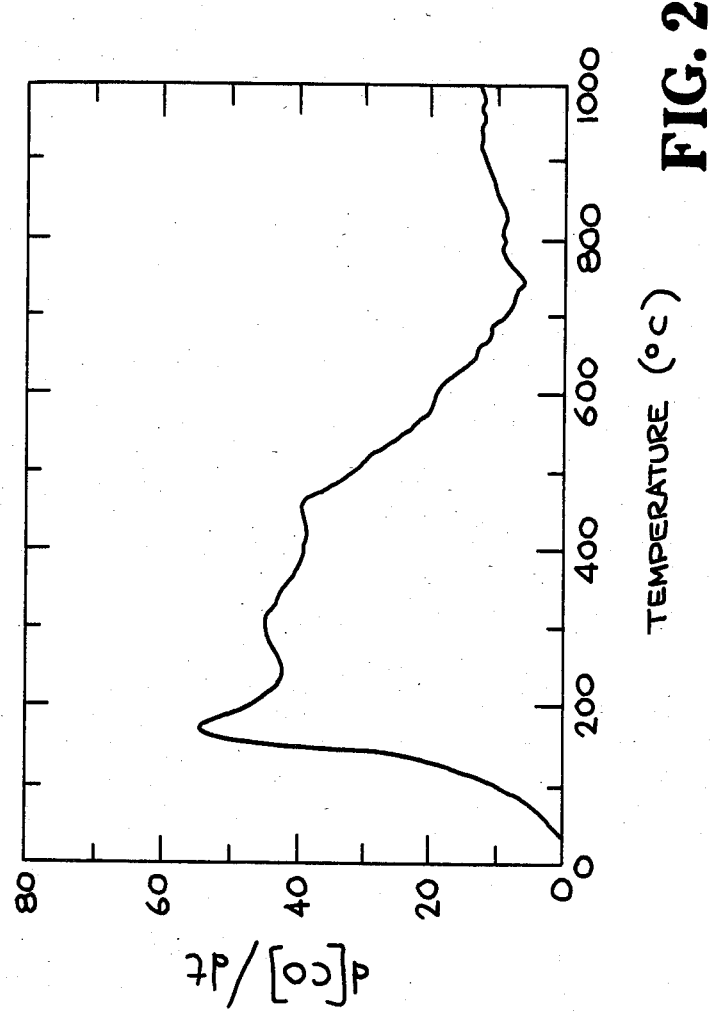
FIG. 2 illustrates an example of an oxygen thermogram of a material sample produced in accordance with the invention.

The temperature-programmed mode, described above, quantitates the released oxygen from the sample as a function of temperature, thus identifying individual compounds and classifying groups of oxygenated compounds according to the temperatures at which they decompose in either reactive inert atmospheres. By use of this mode, an oxygen thermogram of the sample can be obtained. An example of an oxygen-thermogram of a benzene/methanolchloroform extract of a filter sample is illustrated in FIG. 2. This thermogram shows several notable features. There is relatively little low-temperature volatile organic oxygen; and although the choice of a low-temperature interval is subjective, only a small fraction of Op is evolved below 150° C. The thermogram shows that several dominant types of oxygenated material could exist in the sample, each having a characteristic temperature interval in which it evolves. The rising signal observed above 740° C. is thought to be due to the decomposition of oxygen in organic material that carbonized during analysis—a plausible conclusion in light of char formation during analysis.

The method and apparatus of this invention has been experimentally verified utilizing a variety of sample materials. The results of this experimental verification is described in report LBL-16103, "Determination Of Organic Oxygen In Ambient Particulate Matter", W. H. Benner et al, published August 1983, Lawrence Berkeley Laboratory, University of California.

It has thus been shown that the present invention provides a technique that is sensitive enough to detect microgram quantities of pyrolyzable oxygen in ambient particulate matter. The technique can also be used to quantitate organic oxygen in solvent extracts of ambient particulate matter. By this technique, oxygen thermograms show distinguishable features that can be used to characterize general types of oxygenated material in ambient particulate matter. The oxygen analyzer of this invention has the capability of identifying and classifying microgram quantities of oxygen in ambient particulate matter, with a sensitivity, based on experimental testing, that is about two times greater than the known oxygen analyzer devices.

The apparatus and method of this invention has been described with respect to its application for analyzing oxygen compounds which are difficult to detect in samples of ambient particulate matter. However, it might be used for analyzing other compounds, and it is not intended to be limited to the specific materials, parameters, etc. described above. Also, the types of filters and scrubber described are not intended to be limiting.

While a specific embodiment of an apparatus has been illustrated and described for carrying out the oxygen analysis in accordance with this invention, modifications and changes of the apparatus, parameters, materials, etc. will become apparent to those skilled in the art, and it is intended to cover in the appended claims all such modifications and changes which come within the scope of this invention.

What is claimed is:

1. An oxygen analyzer comprising:
   a pyrolysis tube,
   a temperature programmed oven through which said pyrolysis tube extends,
   a pyrolysis oven into which said pyrolysis tube extends,
   a quantity of granular carbon located in a portion of said pyrolysis tube within said pyrolysis oven and adapted to be heated to a temperature of about 1135° C. by said pyrolysis oven,
   means for moving a sample of material to be analyzed through said pyrolysis tube so as to position a sample of material to be analyzed in either said temperature programmed oven or said pyrolysis oven,
   a computer operatively connected to said temperature programmed oven for increasing the temperature of said oven as a function of time,
   detector means operatively connected to said pyrolysis oven to receive gaseous material from said oven, said computer also being operatively connected to said detector means so as to receive input signals from said detector means relative to measurement of gaseous material directed through said detector means, and
   means for backflushing said pyrolysis tube with nitrogen gas,
   whereby, a sample of oxygen containing material is decomposed and converted to carbon monoxide witin at least one of said ovens for subsequent detection such that microgram quantities of oxygen in a sample being analyzed can be determined.

2. The oxygen analyzer of claim 1, wherein said means for backflushing said pyrolysis tube includes a nitrogen gas supply and a single multiport valve interconnected at least between said pyrolysis tube and said nitrogen gas supply.

3. The oxygen analyzer of claim 2, wherein said backflushing means additionally includes a filter and scrubber assembly positioned intermediate said nitrogen gas supply and said multiport valve, and valve means for directing nitrogen gas from said supply through said filter and scrubber assembly and/or directly to said multiport valve.

4. The oxygen analyzer of claim 1, additionally including means located intermediate said pyrolysis oven and said detector means for converting the carbon monoxide to carbon dioxide, which is detected and measured in said detector means.

5. The oxygen analyzer of claim 1, wherein said means for moving a sample of material through said pyrolysis tube includes magnetic means including a plunger which is located within said pyrolysis tube and adapted to be moved through said pyrolysis tube so as to position a sample of material to be analyzed in either said temperature programmed oven or said pyrolysis oven.

6. The oxygen analyzer of claim 5, wherein said magnetic means is removably secured to said pyrolysis tube to allow insertion of a sample of material to be analyzed into said tube.

7. The oxygen analyzer of claim 1, wherein said computer is constructed to receive input signals from said temperature programmed oven relative to the temperature of said oven and to direct signals to said temperature programmed oven to increase the temperature of said oven as a function of time.

8. The oxygen analyzer of claim 7, wherein said temperature programmed oven is constructed to be controlled by said computer through a time selected temperature range of from room temperature to about 1135° C.

9. The oxygen analyzer of claim 8, wherein said temperature programmed oven is constructed to heat from room temperature to about 1135° C. through a time sequence increase of 30° C. per minute.

10. The oxygen analyzer of claim 1, additionally including means for performing a check out of said pyrolysis tube and said detector means by inserting known quantities of known gases thereinto.

11. The oxygen analyzer of claim 1, wherein said backflushing means includes a multiport valve selectively connected to be in fluid communication with at least said pyrolysis tube, a nitrogen gas supply and a backflush vent; and said multiport valve being additionally selectively connected to said detector means.

12. The oxygen analyzer of claim 11, wherein the nitrogen gas supply is connected directly to said multiport valve and/or connected to said multiport valve through a filter and scrubber assembly, and additionally including control means for directing gas from the nitrogen gas supply to said multiport valve.

13. The oxygen analyzer of claim 11, additionally including means for injecting a selected gas into said pyrolysis tube, means for injecting a selected gas into said detector means, and means for directing a calibration gas into said detector.

* * * * *